US005700274A

United States Patent [19]
Feaster

[11] Patent Number: 5,700,274
[45] Date of Patent: Dec. 23, 1997

[54] REFRACTIVE SURGERY KNIFE

[76] Inventor: Fred T. Feaster, 4417 Overton Crest, Fort Worth, Tex. 76109

[21] Appl. No.: 543,213

[22] Filed: Oct. 13, 1995

Related U.S. Application Data

[63] Continuation-in-part of Ser. No. 127,821, Sep. 28, 1993, Pat. No. 5,458,610.

[51] Int. Cl.$^6$ ................................................. A61B 17/32
[52] U.S. Cl. ........................... 606/167; 606/166; 30/320; 128/305
[58] Field of Search .......................... 606/166–167, 606/170, 177, 107

[56] References Cited

U.S. PATENT DOCUMENTS

| | | | |
|---|---|---|---|
| 4,499,898 | 2/1985 | Knepshield et al. | 606/170 |
| 4,516,575 | 5/1985 | Gerhard et al. | 606/170 |
| 4,526,171 | 7/1985 | Schachar | 606/172 |
| 4,534,348 | 8/1985 | Fedorov et al. | 606/166 |
| 4,602,630 | 7/1986 | Anis | 606/184 |
| 4,619,259 | 10/1986 | Graybill et al. | 606/184 |
| 4,768,509 | 9/1988 | Grosvenor et al. | 606/166 |
| 4,884,569 | 12/1989 | Fedorov et al. | 606/166 |
| 5,201,747 | 4/1993 | Mastel | 606/166 |
| 5,219,350 | 6/1993 | Emerson | 606/107 |

FOREIGN PATENT DOCUMENTS

| | | | |
|---|---|---|---|
| 1463253 | 12/1986 | U.S.S.R. | 606/167 |
| 2113550 | 8/1983 | United Kingdom | 606/167 |

*Primary Examiner*—Michael Buiz
*Assistant Examiner*—Nancy Mulcare
*Attorney, Agent, or Firm*—Arthur F Zobal

[57] ABSTRACT

The refractive surgery keratotomy knife has a handle with a footplate and a holding member for receiving and holding a flared surgical blade fixed to the handle and knife body. The footplate is adapted to be placed against the cornea of the eye. The blade is held by a blade support with the cutting edge of the blade extending beyond the footplate for forming an incision in the cornea of the eye by pressing the blade directly into the cornea tissue.

9 Claims, 11 Drawing Sheets

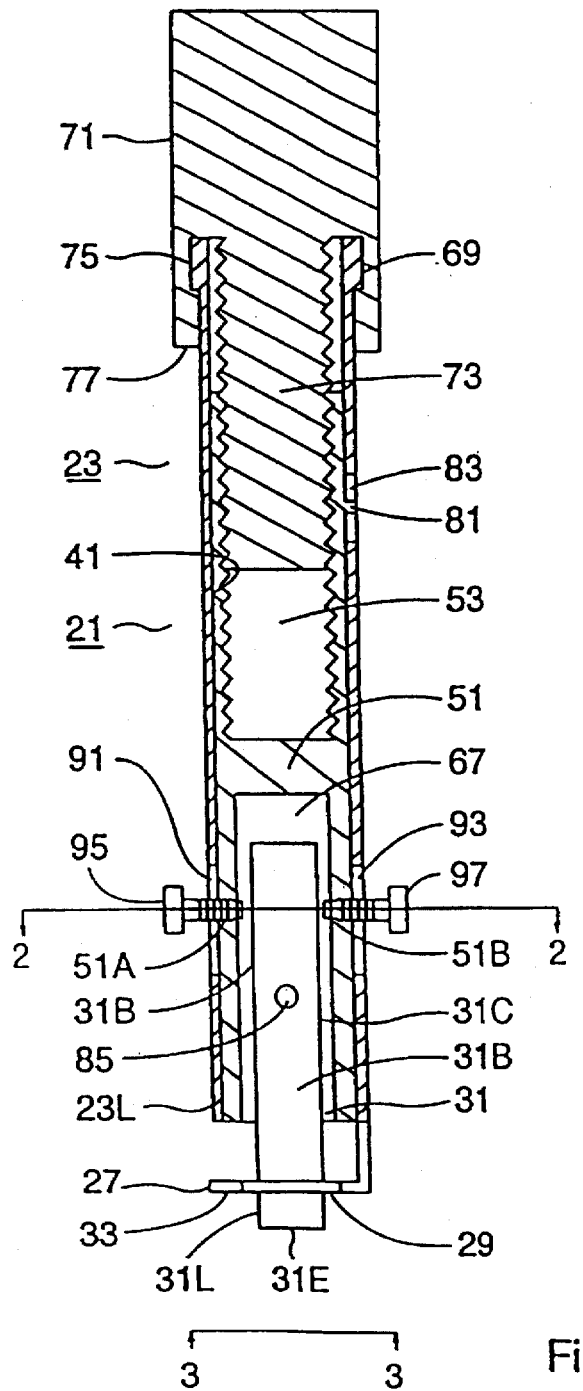
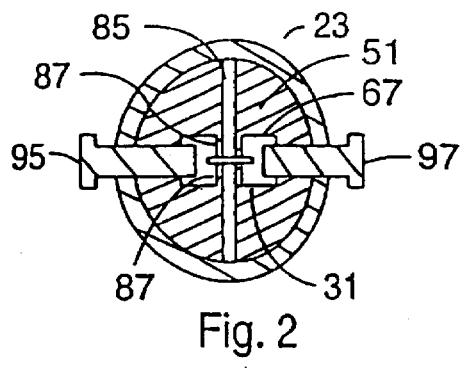
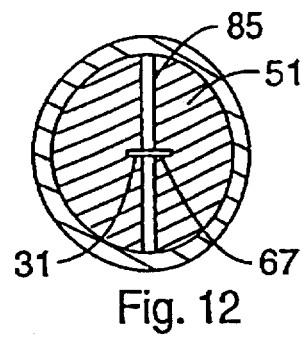
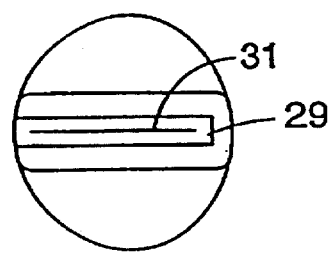
Fig. 2
Fig. 12
Fig. 3
Fig. 1

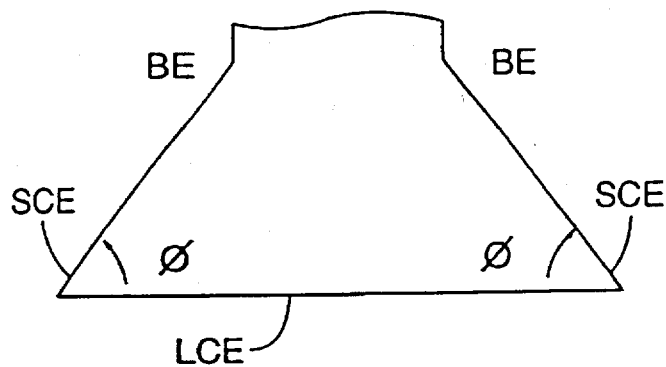
Fig. 8    Fig. 4
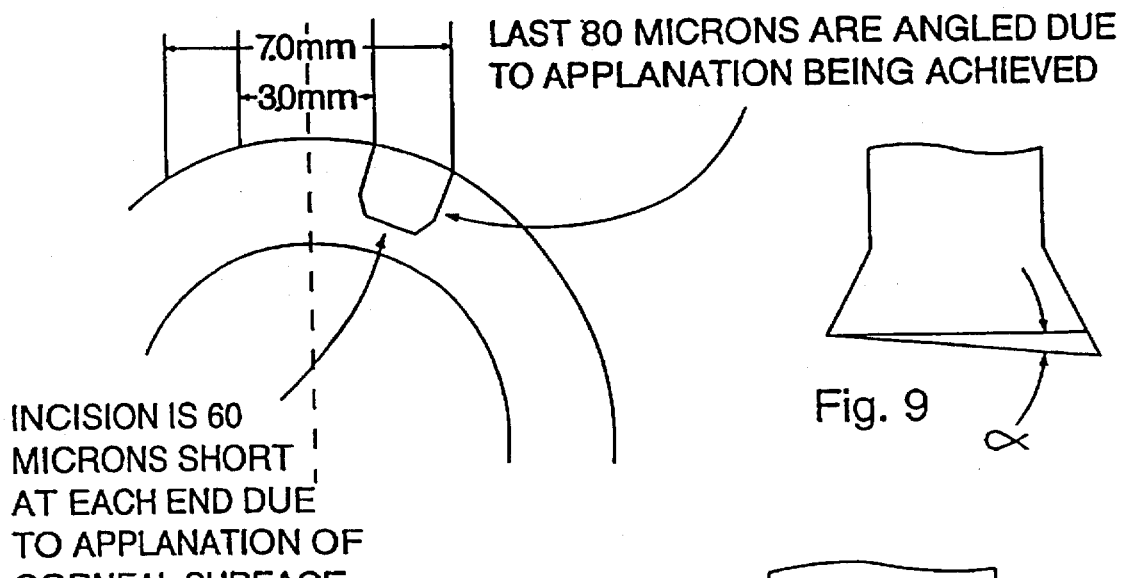
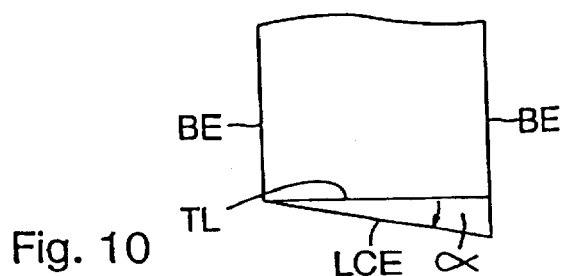
Fig. 11
Fig. 9
Fig. 10

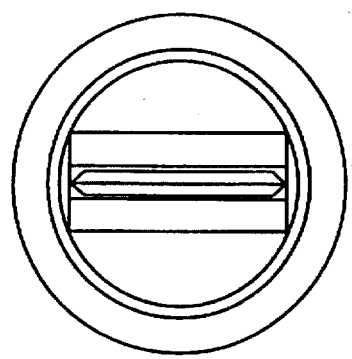
Fig. 28
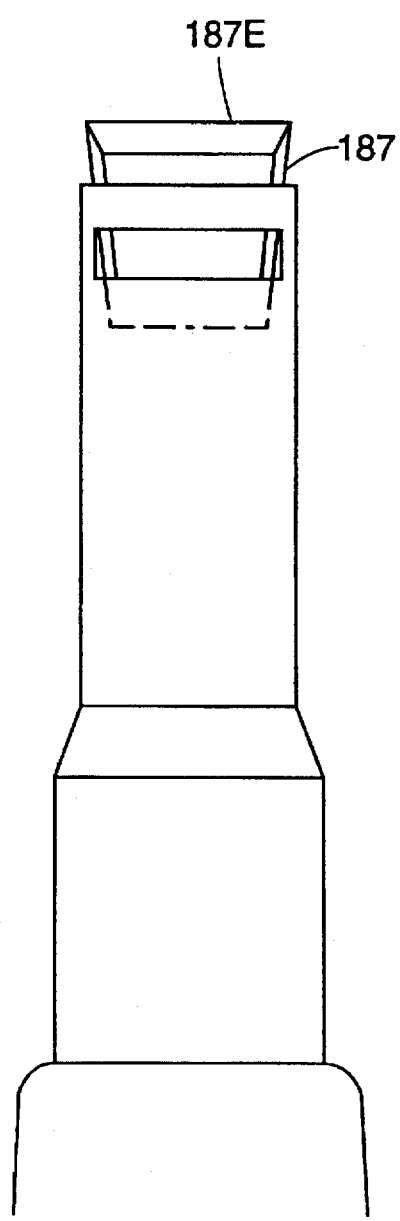
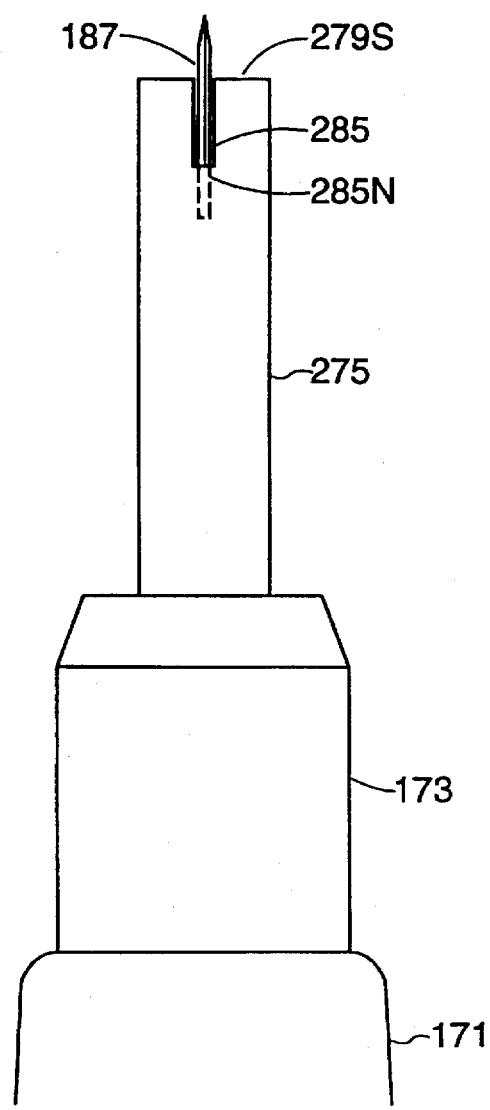
Fig. 26  Fig. 27

Fig. 31
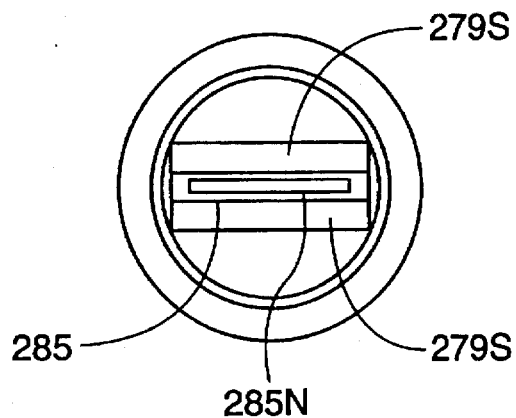
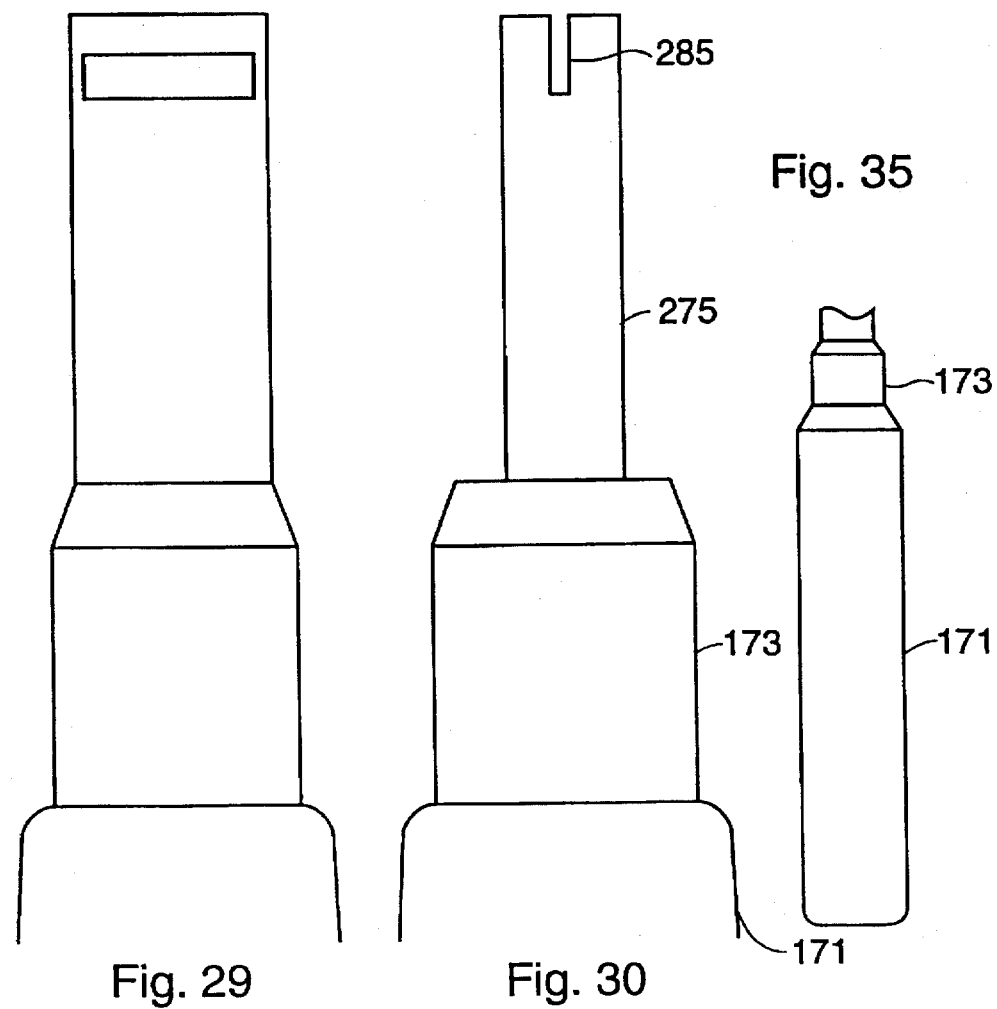
Fig. 29   Fig. 30   Fig. 35

REFRACTIVE SURGERY KNIFE

This application is a continuation-in-part of U.S. patent application Ser. No. 08/127,821, filed Sep. 28, 1993, now U.S. Pat. No. 5,458,610.

BACKGROUND OF THE INVENTION

1. Field of the Invention

The invention relates to a refractive surgery keratotomy knife for manual incisional keratotomy.

2. Description of the Prior Art

Of the many methods of refractive surgery currently available, manual incisional keratotomy, including radial keratotomy and astigmatic keratotomy, have the longest history and are the most established.

The procedure consists of marking the central optical zone of the cornea with a round optical zone marker which outlines and indicates the central area of the cornea which is to be left uncut. Incisions with a surgical knife are then made into the substance of the cornea outside of and up to the central optical zone in a radial configuration (or tangential orientation). The incisions have the effect of altering the curvature of the cornea to a flatter curvature thereby reducing myopia or astigmatism.

The procedure initially was performed in Japan by Sato who performed the procedure as an intraocular procedure making radial incisions on the posterior, entothelial corneal surface in a radial fashion. This technique however, eventually resulted in an unacceptably high incidence of corneal swelling and decompensation resulting in it being abandoned.

Radial and astigmatic keratotomy were then refined in Russia notably by Fyodorov who popularized the technique of cutting the anterior surface of the cornea from the periphery towards the center with incisions beginning actually outside the clear cornea, cutting across the limbus (the junction of the sclera and clear cornea), with the incisions continuing toward the center stopping at the edge of the central optical zone which was left uncut. This technique known as the Russian technique, is described as cutting "uphill" since the scalpel blade is drawn from the relatively flat peripheral cornea to the steeper, central cornea.

This technique has been refined and revised by multiple investigators in this country resulting in a technique in which incisions are made from the central cornea outwardly in a radial fashion toward the corneal periphery. This technique, known as the American technique, has the advantage of cutting away from the optical zone, thereby avoiding inadvertent cutting of the central optical zone which could possibly adversely affect vision.

Both of the currently practiced techniques, the central, uphill-cutting Russian technique, or the peripheral down-hill cutting American technique, require that the scalpel blade be manually drawn along the cornea surface to produce the corneal incision. More specifically, current radial keratotomy knives are designed with footplates which are placed on the corneal surface, between which and below which a cutting portion of the scalpel blade extends to enter into the cornea. The scalpel is placed with the footplates resting on the corneal surface with sufficient pressure to flatten or applanate the underlying cornea so that the scalpel blade cuts the applanated underlying cornea at right angles. The scalpel blade, which is today generally made of gemstone such as diamond, is set a precise distance extending beyond the footplates to produce an incision of a specific, desired depth in the tissue.

Current radial keratotomy scalpels require that the knife blade be set into the corneal tissue (with depth controlled by the footplates) at either the most peripheral or most central aspect of the intended incision, and then passed under manual control along the corneal surface either from peripheral-to-central, or central-to-peripheral to accomplish the incision. That is to say, the scalpel must be drawn along the corneal surface in order to make the incision. This requires extreme control of the scalpel by the operating surgeon at all times during the incision. Direct visualization through the operating microscope of the scalpel as it is passed across the cornea making the incision is necessary at all times. Due to the exquisite sharpness of the scalpel blade, it is not uncommon for incisions to be irregular, non-linear, of variable depth, and to possibly extend more peripherally, or centrally into the optical zone, than is desired, thereby producing imprecise and possibly damaging incisions.

That is to say, knives in current surgical techniques, are likely to produce less than ideal incisions from the precise depth and length that are desired. In fact, it will be shown that these knives used in keratotomy have inherent design limitations that produce less than the ideal incisions of precise depth and length and profile configuration that are desired. As will be taught below, a new surgical technique and keratotomy knife design, in which the scalpel blade, having a dimension comprising essentially the entire length of the desired incision, is pressed directly into the corneal tissue, thereby cutting the full length of the incision simultaneously (all at once), is superior to the current surgical techniques and blade designs requiring that the knife be drawn across the surface of the cornea As radial keratotomy has been refined, investigators, particularly Lindstrom, have determined that maximum refractive correction can be accomplished with incisions that are considerably shorter than previously used and thought necessary. Whereas, in the past, incisions were made to extend and involve the cornea from the central, uncut optical zone, to the corneal periphery just inside the limbus, Lindstrom has determined that adequate and maximum refractive correction can be obtained using incisions no more than 7 to 8 mm. to total length in any particular meridian, thereby requiring a single incision on either side of the optical zone in any meridian of a maximum length of about 2.0 to 2.5 mm. rather than the previously made incisions which were frequently 4 to 5 mm. or longer.

The fundamental rationale, therefore, for small incision radial keratotomy, is that clinically it has been observed, notably by Lindstrom, that incisions that extend peripherally beyond the 7 mm. optical zone mark have very little additional effect in reduction of myopia compared to incision that extend up to or just beyond the 7 mm. optical zone. More specifically, Lindstrom has observed that no more than approximately 0.5 diopters of additional total effect is achieved by making incisions that extend out to or near the limbus (in an 8 cut procedure). Further, Lindstrom has in fact observed a decrease in achieved reduction in myopia when the limbus is actually cut. The theoretical prediction that small incisions should give virtually full correction was to my knowledge, first made by Dr. Ron Schachar in his book, *Understanding Radial Keratotomy*, Chapter 2, pp. 12–28, LAL Publishing, 1981, Denison, Tex.).

Therefore, it appears that an incision need not extend beyond approximately the 7 mm. optical zone. This surgical technique of incisional keratotomy has been referred to as "mini" radial keratotomy or "mini" RK.

With the discovery and recognition of the fact that shorter incisions (mini RK) can accomplish full refractive correction, it can now be appreciated that new and different innovative surgical instrumentation and techniques can possibly be utilized. More specifically, a change in surgical technique and instrumentation would be particularly desirable and advantageous, if in addition to incorporating the concepts of mini RK, the new instrumentation and surgical technique would improve the reliability, ease of performance and safety of radial keratotomy.

It is the object of the invention to provide a new refractive surgery keratotomy knife, and a new refractive surgery technique for manual incision keratotomy, such that the incision is made using a technique in which the scalpel knife, having a blade with the cutting edge dimension comprising essentially the full linear dimension of the desired incision, is pressed directly into the corneal tissue rather than drawing the knife across the corneal surface as is common in current techniques. The knife design, in addition to having a blade dimension of essentially the full length of the linear dimension of the desired incision, also contains a flair configuration (seen in profile). In addition, the more vertical edge of the blade may have a small length of cutting edge near the bottom of the blade. Finally, the blade may be angulated relative to the footplates to produce a more ideal incision. The angulation relative to the footplates may be either fixed, or adjustable.

The radial keratotomy knife and surgical design will be described, explained, and derived in this discussion below.

If one considers that the smallest, generally accepted optical zone necessary is 3 mm., then the longest incision in any hemi meridian (on either side of the optical zone) necessary to accomplish virtually maximum myopic reduction is 2 mm. (the chord length from the edge of the 3 mm. optical zone to the 7 mm. optical zone in each hemi meridian). This further indicates that the blade length necessary to cut the full incision length simultaneously (all at once) is a minimum of 2 mm. in length. However, it further indicates that the blade length need not be any longer than approximately 2.5 mm. in length (if one considers the increased surface length due to the arcuate curvature of the corneal surface, and the slightly imperfect tissue incision profile produced at the extreme ends of the incisions to be discussed later in more detail).

It is possible to consider blade lengths of shorter dimension in dealing with patients who require a larger than 3 mm. optical zone for correction, so that possibly blade lengths as short as 1 mm. or less might conceivably be used. However, it would seem reasonable and practical to consider one blade length that would cover all incision lengths necessary, including the longest of 2 mm. A blade length of between 2.2 mm. to 2.5 mm. is considered to be optimal for reasons to be discussed subsequently.

After accepting that small incision radial keratotomy (mini RK) is optimal for many reasons, it is important to consider exactly what the shape of the "ideal" incision is. It is a general consensus of refractive surgeons that the incisions made with current instrumentation and techniques produce a considerably less than optimal, or ideal incision. Several incision profile characteristics of the "ideal" incision are apparent. They are:

1. The incision be of optimal length (neither too long nor too short) to accomplish the desired refractive reduction.
2. The incision have central and peripheral ends which are perpendicular to the overlying (anterior) corneal surface (to achieve maximal depth with minimal tissue cutting).
3. The incision be a uniform percentage depth of the total corneal thickness at any given location along the length incision. That is to say, for example, the ideal incision would be a constant 90 to 95% depth of the total corneal thickness at any site along its length.

With the parameters of the "ideal" incision in mind, it is clear that the incisions currently being produced with "modern" RK techniques are considerably less than ideal. Both the Russian-cutting (peripheral-to-central) or American-cutting (central-to-peripheral) techniques produce incisions that have a "ski" configuration, as shown in FIGS. 16–19, which is particularly a concern when it occurs at the central end of the incision (as it does in the American technique), since it means that the full depth of incision is not accomplished at the most critical central portion of the incision, immediately adjacent to the uncut central optical zone. Until now, the phenomenon of "skiing" at either end of the incision has been erroneously attributed to the effect of tissue compression of the corneal tissue by the footplate, with the explanation being that the corneal tissue is compressed and therefore not cut. It will be shown below that tissue compression is not the primary cause for the "skiing" phenomenon in radial keratotomy incisions. Rather, the "skiing" phenomenon is due to a change in tissue shape of the corneal curvature associated with the applanation process resulting in a translation or displacement of the tissue form a naturally curved configuration to a flat, applanated corneal configuration as a result of footplate pressure from the knife. As will be discussed, tissue resistance to cutting by the scalpel blade can also produce applanation of the corneal curvature.

In addition to the "skiing" at the central and peripheral ends of the incision, it is also obvious that the incisions made with current techniques are a variable percentage depth relative to the total corneal thickness at any spot along the cornea (FIGS. 17 and 19). This is unavoidable due to the current techniques not being able to compensate well for the known progressive thickening of the cornea from the center to periphery. All incisions made with the current, modern radial keratotomy knives are of a fixed depth relative to the overlying cornea surface which is flattened or applanated by the knife footplates during the incision-making process.

One way to overcome this fundamental design limitation in the current keratotomy instrumentation, is to use a knife design in which the portion of the blade which cuts the deepest-most aspect of the incision is angulated relative to the bottom of the overlying applanating footplates so that the knife compensates by means of its angulation relative to the footplates for the anatomically progressively increasing corneal thickness peripherally.

The blade angulation feature implies that the blade have an elongated edge length for cutting the incision simultaneously (all at once), the elongated cutting edge of the blade, making the deepest part of the incision simultaneously throughout the incision. This requirement eliminates blade designs in which the cutting edge terminates in a single, sharp point. Clearly, a single, sharp point design cuts the deepest portion of the incision only at one point which is fixed and does not vary in depth from the overlying corneal surface. This is a fundamental design limitation of pointed or nearly pointed blade designs which must be drawn across the corneal surface the length of the incision to produce the incision.

Finally, the desirability of making the incision with a single "stab-in" cutting technique, cutting the full and entire length of the incision at one time is desirable since it eliminates or greatly minimizes variations in incision length, depth and straightness due to individual surgical skill and technique.

As mentioned above, the effect of applanation on determining the configuration of the incision profile is not fully appreciated. If it is assumed for the sake of discussion, that there is minimal or no tissue resistance to cutting, then it can be seen that when the cutting blade is placed on the corneal surface, and is pressed into the corneal tissue, it will penetrate and cut into the tissue to a considerable depth prior to the corneal surface being completely applanated. One can readily appreciate that with the knife blade extended below the applanation footplate, when it is placed on the corneal surface, it achieves a certain depth of tissue penetration prior to the applanation footplate contacting the corneal surface and producing a flat, applanated corneal shape. This is true of both a pointed design, and a design with an enlongated cutting edge producing the deepest portion of the incision simultaneously along the entire incision length. It therefore becomes necessary to determine exactly how corneal tissue is applanated and to what extent. Calculations indicate several interesting and possibly surprising facts in this regard.

First, a 3 mm. optical zone marker when placed on the normally curved (non-applanated) corneal surface, produces a mark which encloses a cord length of 3 mm. It should be clearly understood that the actual surface length of cornea thus marked (the are of the curved corneal surface), is not 3 mm. in length. Similarly, a 7 mm. optical zone marker marks a location on the curved anterior corneal surface which has a cord length of 7 mm., again, which encloses an arc of corneal surface tissue of a greater length. This is significant because the 2 mm. maximum length of incision required in one meridian from a 3 mm. optical zone mark to a 7 mm. optical zone mark, although measuring a chord length of 2 mm. actually requires incision along the curved anterior corneal surface which is somewhat greater in length. Calculations indicate that if you assume an anterior corneal radius of curvature of 7.7 mm., the actual curved anterior corneal surface length (surface arc length) between the 3 mm. and 7 mm. optical zone, is not 2 mm., but is 2.12 mm. This difference of 0.12 mm. (120 microns) is significant because it basically gives the length of that arcuate, curved anterior corneal surface when it is changed by applanation from a curved to a flat surface. That is to say, when the curved corneal surface is rendered flat, by the applanation footplates of the knife, the resultant length of the applanated tissue will be 2.12 mm., not 2.0, as might be expected using simply the chord length. Therefore, the knife blade length necessary to cut an applanated (flat) cornea, having a chord length of 2 mm. (assuming a radius of curvature of 7.7 mm.) is 2.12 mm., not 2.0 mm. Since we know that during some portion of the cutting process, the tissue if applanated, the knife will be required to cut the full applanated length of 2.12 mm. if the full length of the desired incision is to be accomplished. It is for this reason, therefore, that a knife blade of greater than 2 mm. length is necessary. The absolute minimum would be 2.12 mm. in length, assuming one cuts up to the 7 mm. optical zone mark. Lindstrom's protocol recommends cutting through the 7 mm. optical zone mark on the cornea which then adds approximately 0.5 mm. of additional length to the incision. It is for this reason therefore, that a blade length of 2.5 mm. is recommended as a length which would encompass and satisfactorily make incisions including the shortest required incision length (approximately 1 mm.), to the longest required (2.12 mm., not the 2 mm. originally presented earlier in this discussion).

Considering that the knife blade is cutting into tissue to a considerable depth prior to the surface being applanated by the footplate (assuming no tissue resistance to cutting), it is necessary to determine how much displacement is produced in the applanation process by the footplates themselves. Calculations indicate that again, assuming an anterior curvature of 7.7 mm., an 80 micron tissue displacement or depression (not compression) downward of the corneal tissue must occur for the anterior corneal surface to be applanated over the previously described distance between the 3 mm. and 7 mm. optical zone marker. Therefore, complete applanation is accomplished during cutting only the last (deepest) 80 microns of tissue. If one assumes a central corneal thickness of 600 microns, then 13.3% of the tissue is cut after applanation. Therefore, one can see that the ideal situation of no tissue resistance, a considerable percentage of the tissue cutting is accomplished prior to applanation. This is an important fact to understand. However, as will be shown subsequently, this phenomenon is relatively inconsequential and can easily be adjusted for with surgical technique and knife blade design.

Since approximately 85% of the tissue incision is made prior to applanation, it can be anticipated that neither the central nor the peripheral end of the incision will be perfectly perpendicular to the anterior corneal surface throughout the entire depth. This is because incisions perpendicular to the corneal surface can be accomplished only when the corneal surface is applanated. Therefore, one can understand that the edges of the anterior 85% of the incision will be slightly non-perpendicular to the anterior corneal surface. However, once applanation is accomplished (during the last approximately 15% of the incision), the incision will be perpendicular to the anterior corneal surface. This will have the effect of producing a definite change in angulation in the depth of the incision at the central and peripheral ends of the incision (FIG. 12).

Although once the tissue is applanated, the blade achieves the desirable effect of perpendicularity of the incision to the anterior corneal surface, it will have the less desirable effect of "shortening" the length of the incision in the tissue (see FIG. 11). Calculations indicate that in the ideal, no-tissue-resistance-to-cutting situation, the "shortening" of the incision length at the deepest, approximately 15% of the incision (when the incision is accomplished under applanation) will produce a shortening at each end of the incision of approximately 60 microns (again assuming a radius of corneal curvature of 7.7 mm.). This "shortening" of the incision at its greatest depth can be compensated for by producing an appropriate blade configuration and surgical technique.

It is intended to have a blade design such that the entire length of the bottom of the blade is a cutting edge with the vertical edges being generally blunt preventing any cutting of the tissue by the blade beyond the dimensions of the bottom of the blade itself. The scalpel blade may have a generally rectangular shape or profile as viewed from the side. However, if the blade configuration has a "flare" configuration as seen from the side (see FIG. 8), it is possible to make the vertical edge of the knife blade sharp to a vertical height of approximately 60 microns on either end of the blade (actually approximately 100 microns along the angulated vertical edge). Once the knife blade is placed within the tissue and the tissue is applanated, the incision can be "lengthened" at its greater depth by "jiggling" the blade (moving the blade forward and backwards) parallel to the long axis of the incision while the footplates applanate the overlying cornea and the blade is in place within the incision. This will have the effect of cutting the deepest aspect of the tissue at the ends of the incision with the small, sharp length of the vertical blade on either end. However, since the majority of the vertical blade will be non-cutting, the blade will not move generally beyond the initial linear dimension of the incision. The slight give of the corneal tissue at each end of the incision will allow for a 60 micron movement forward and backward within the tissue incision, but prevent any major movement of significance. Therefore, by using a "jiggling" technique, the incision can be made the full desired length.

The above description of cutting of corneal tissue assumes the ideal situation of no tissue resistance. If the more realistic situation of normal tissue resistance to the cutting of corneal tissue is assumed, then the effectiveness of producing a more theoretically ideal incision is changed. Specifically, since the corneal tissue will produce some resistance to cutting, it can be anticipated that when a blade with an elongated cutting edge dimension (simultaneously, full-length-cutting design) is set on the curved, corneal surface), normal tissue resistance will cause the surface to be applanated by the cutting edge along a considerable length of the blade as it rests along the intended corneal incision on the corneal surface (possibly the entire length, prior to any cutting actually taking place). That is to say, that the cutting edge of the blade may rest on the curved corneal surface, and due to tissue resistance, flatten or applanate the corneal surface prior to cutting beginning due to tissue resistance. Here again, the inherent design superiority of the elongated cutting edge blade design over the pointed blade design is seen. It can be calculated that a depression of 100 microns is necessary to fully applanate the entire length of 2.5 mm. cutting edge. Therefore, in actual reality, it can be appreciated that it is entirely possible that the elongated cutting edge blade design can very possibly produce a theoretically ideal incision configuration with the edges perpendicular to the overlying surface from the outset of initiation of the incision. This is in stark contrast to the pointed blade designs which can be anticipated to encounter substantially less tissue resistance at the sharp tip, thereby producing considerably less tissue applanation prior to the blade cutting deep enough into the corneal tissue to applanate the corneal tissue with the footplate of the knife.

To summarize then, the small incision simultaneously full-length-cutting knife blade design has some unexpected yet very understandable and desirable characteristics that are completely different from radial keratotomy knife designs as they are currently used. First, the length of the incision is not 2.0 mm. as might be expected by casual inspection, but rather 2.12 mm. A blade length of approximately 2.5 mm. is recommended to ensure complete, adequate incision length.

Second, the full-length cutting design produces approximately 85% of this incision prior applanation of the overlying corneal surface in the ideal, no tissue resistance to cutting situation. This has the minor consequences of producing ends to the incision which are just slightly non-vertical until approximately the last 15% of the deepest portion of the incision, at which time an incision with perpendicular sides is accomplished. However, this is accomplished at the expense of shortening the incision (approximately 60 microns at each end of the incision). This can be compensated for easily by producing a knife blade design which has a slight flair with a cutting edge of approximately 100 microns along each relatively vertical edge. The incision is then made the full length by a slight "jiggle" when the knife blade is set in the tissue to its full applanated depth.

As mentioned also, however, a more realistic situation of tissue resistance to cutting which is more accurate in the reality of radial keratotomy surgery, may result in the full-length incision blade design to produce the ideal incision from the outset due to the initial tissue resistance which results in full applanation and flattening of the corneal surface prior to initiation of the tissue cutting.

There are, herein presented, new knife designs and a new surgical technique for manual incision radial keratotomy. The knife design comprises a blade with an elongated cutting edge of a dimension constituting virtually the entire linear extent of the desired excision. In order to produce a maximally ideal incision, the knife blade has a profile configuration which is a "flare" shape with a short distance of sharp cutting edge being present along the lower aspect of the relatively vertical edges. In addition, the knife blade may be angulated relative to the bottom of the overlying footplates, to produce an incision of consistent, constant percentage depth relative to the overlying cornea. This angulation relative to the overlying footplates may be fixed in amount, or adjustable by a mechanism contained within the knife handle. The knife design further constitutes applanating footplates between which and beyond which the blade is extended to a precise depth for producing an incision of a precise, desired depth in the corneal tissue.

In a preferred embodiment, the cutting edge of the blade will have a length of 2.5 mm. with sharp cutting edge along its entire extent. The blade will have a flared profile with a cutting edge along the more vertical sides of approximately 100 microns at each end. The blade cutting edge may be formed of diamond with a thickness of 100 microns. The blade will have an angulation relative to the overlying footplate of approximately 1 to 2 degrees. The blade formed of diamond gemstone will have a thickness of 100 microns. The knife will have applanation feet or a single plate with a central separation or opening to allow the blade to pass through the footplates and beyond them. The angulation of the blade relative to the overlying footplates may be fixed or adjustable by a mechanism contained in the knife handle.

The knife is intended to be used with a new surgical technique consisting of placing the entire cutting edge length of the bottom of the knife blade on the corneal surface and pressing directly into the corneal tissue, thereby cutting the tissue to the full and desired depth as controlled by the bottom of the overlying footplates. When the blade is pressed into the greatest depth of the tissue to be accomplished, it may be felt necessary, in order to produce the most ideal incision possible, to "jiggle" or move the knife blade parallel to the length of the incision while the blade is set as deep as possible into the incision. This simultaneous, all-at-once incision-cutting technique differs completely from the currently used technique of drawing the blade along and across the corneal surface. The advantages of both of the herein described knife design and surgical techniques are considerable and are anticipated to improve the incision configuration, ease of producing the incision, and increase the safety of incisions thus made. It can therefore be seen that this new radial keratotomy knife and surgical incision technique for manual incision radial keratotomy have considerable advantages and unique features which make this knife and surgical technique superior to current knife designs and techniques.

SUMMARY OF INVENTION

To provide a new refractive surgery keratotomy knife for manual incision keratotomy such that the knife produces its incision in the cornea without being drawn across the surface of the cornea as is done in current and conventional techniques.

SURGICAL TECHNIQUE

The patient is prepped in the usual manner for ocular surgery after the eye has been rendered anesthetic with topical drops. The patient is positioned under the operating microscope and the eyelids separated with an eyelid speculum. With the patient fixating on the fixation light of the operating microscope, the central optical zone size specific to this patient's procedure is marked with an optical zone marker gently pressing on the corneal surface to produce an adequate demarkation indentation. A radial keratotomy incision marker (typically 4 cut or 8 cut marker) is centered on the patient's cornea and the corneal surface demarkated with the radial marker to locate the sites for the radial incisions. Additional astigmatic T-cut (tangential) marks may also be placed. With the patient fixating at the operating microscope fixation light, the scalpel blade (which has its blade extension previously set based on the patient's corneal thickness measurements at the site of each intended incision) is set on the corneal surface along the demarkated radial incision mark. With pressure directly down upon the corneal surface, the blade is pressed into and cuts the corneal tissue until the cornea is fully applanated by the feet of the knife. With the blade held at its greatest depth of cut, the blade is "jiggled" slightly forward and backward parallel to the lines of the incision. The blade is then removed and the subsequent incisions are made in a likewise manner. Typically, the sequence of incisions will progress from superior, to nasal, to inferior with the most temporal incision being made last. After each incision being made in this fashion, the procedure is then terminated. Should astigmatism incision T-cuts be necessary, then they are made usually prior to the radial incision. The T-cuts or tangential incisions are made in a similar, pressed down manner at the location found necessary for the individual patient. Once all T-cut and radial incisions have been accomplished, the eyes are instilled with antibiotic and anti-inflammatory medications and the procedures is terminated.

BRIEF DESCRIPTION OF THE DRAWINGS

FIG. 1 is a partial cross-sectional view of the knife a refractive surgery knife.

FIG. 2 is an enlarged cross-section of FIG. 1 taken along the lines 2—2 thereof.

FIG. 3 is a view of FIG. 1 taken along lines 3—3 thereof.

FIG. 4 illustrates the cutting edge of the blade of the knife.

FIG. 8–10 illustrate different shapes of the blades which may be used in the knife.

FIG. 11 illustrates the shape of an incision formed in the cornea of the eye with a rectangular shaped end.

FIG. 12 is an enlarged cross-section of another embodiment of a refractive surgery knife.

FIG. 26 is another embodiment of the invention wherein the blade is fixed to the handle of the knife.

FIG. 27 is a view of FIG. 26 as seen from the left side of FIG. 26.

FIG. 28 is a view of FIG. 26 as seen from the front end of FIG. 26.

FIGS. 29, 30, and 31 are views of the knife of FIGS. 26, 27, and 28 respectively without the blade in place.

FIG. 35 illustrates the complete handle of the knives of FIGS. 19–34.

DESCRIPTION OF THE PREFERRED EMBODIMENTS

Figure 5:
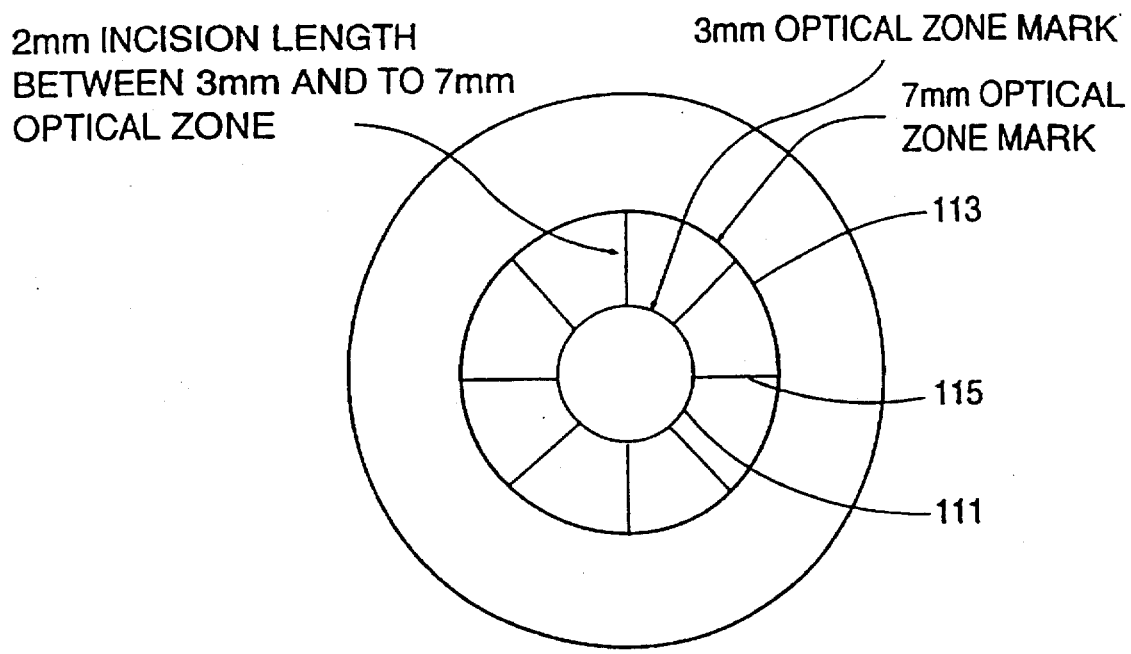
FIG. 5 is an enlarged front plan view of the cornea of the eye.

Referring now to the drawings, a refractive surgery knife is identified by reference numeral 21, it comprises an elongated hollow cylindrical handle 23 or support body with a lower footplate 27 extending transversely to the length of the handle and having a narrow elongated opening 29 formed therethrough for receiving the lower portion 31L of the blade 31 of the knife. The footplate 27 has a bottom surface 33 for engaging the cornea of the eye.

The handle 23 has a hollow cylindrical opening 41 formed therethrough in which is slidably located a cylindrical blade holder 51 having an upper cylindrical opening 53 with threads 55 and a lower opening 67 which is rectangular in cross-section. The upper end of the handle has a flange 69. An adjusting member 71 is provided having a threaded cylindrical shaft 73 which extends into the opening 41 of the handle 23 and is screwed into the opening 53 of the holder 51. The member 71 has a sleeve 75 which surrounds the upper end of the handle 23 and which has an inward extending lip 77 below the flange 69. Rotation of the member 71 in one direction causes the shaft 73 to move the holder 51 away from the lower end 23L of the handle 23 and rotation of the member 71 in an opposite direction causes the shaft 73 to move the holder toward the lower end 23L of the handle 23. The holder 51 has a stud 81 which slides in an elongated slot 83 formed in the wall of the handle 23 to prevent the holder 51 from rotating relative to the handle 23.

A thin rectangular shaped surgical blade 31 is located in the opening 67 and pivotally secured thereto by a pivot pin 85 such that its lower end 31L including its cutting edge 31E extends out of the opening 67. The blade 31 may include a body portion 31B formed of stainless steel and a cutting edge 31E of gemstone such as diamond secured to lower edge of the body portion 31B. The pin 85 extends through an aperture formed through the blade 31. The ends of the pin 85 are supported in apertures formed through member 51.

Washers 87 prevent movement of the body portion 31B of the blade 31 along the pin 85.

By rotating member 71, the holder 51 can be moved toward the footplate to locate the lower end 31L of the blade 31 and its cutting edge 31 through opening 29 and beyond the lower surface 33 of the footplate a desired precise distance for performing surgical procedures on the cornea of the eye.

Formed through the wall of the handle 23 on opposite sides are two elongated apertures 91 and 93. Formed through opposite sides of the member 51 are two threaded apertures 51A and 51B into which two threaded members 95 and 97 are screwed.

The shafts of the members 95 and 97 extend through the openings 1 and 93 to allow member 51 to be freely moved upward or downward relative to the handle 23.

The purpose of the members 95 and 97 is to allow them to be screwed into the opening 67 and to engage opposite edges 31B and 31C of the blade 31 and to securely hold it in place. The members 95 and 97 also can position the blade 31 and hence its lower cutting edge 31E to different angular positions relative to the lower surface of the footplate 31.

Referring to FIG. 5, reference numeral 111 defines the central optical zone of the eye in which radial incisions are to be avoided and reference numeral 113 defines the outer optical zone beyond which radial incisions 115 are desired to be limited, thus the radial incisions 115 are to be made within zones 111 and 113. The diameter of zone 111 is about 3 mm and the diameter of zone 113 is about 7-7.5 mm.

Figure 6:
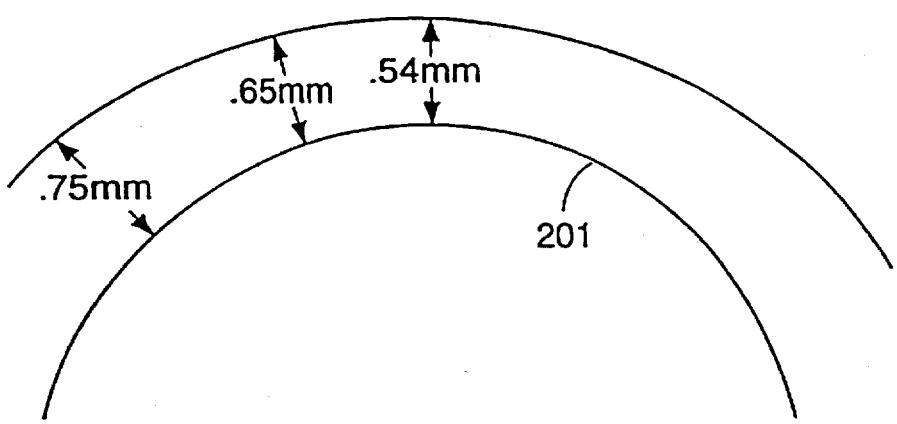
FIG. 6 is an enlarged cross-sectional view of the cornea of the eye.

FIG. 6 illustrates the increase in thickness of the corneal outward from its center point C.

If the cutting edge of the blade 31 is parallel to the lower surface 33 of the footplate 27 then the bottom of the incision will not follow the bottom or posterior surface 201 of the cornea as is optimally desired. This can be avoided by securing the blade 31 in the knife to a position such that its cutting edge is not parallel with the bottom surface of the footplate 27.

This can also be accomplished by using a blade having an angulated cutting edge CE relative to its blunt edges BE as shown in FIG. 10. In FIG. 10 the angle alpha may be of the order of one or five degrees or less relative to a transverse line TL extending perpendicular to each of edge BE. If the blade of FIG. 10 is used, angular adjustment of the blade is not necessary and a knife may be used without the angular adjustment feature as shown in FIG. 12. In this embodiment, the opening 67 is only large enough to receive the blade and does not allow pivotal movement. Means such as the pin 85 is provided for securely holding the blade in the opening 67.

Preferably the cutting edge CE of the blade will have a length about equal to or greater than the surface radial distance or length between zones 111 and 113.

In using the knife, the cutting edge CE of blade 31 is adjusted to the desired distance below the footplate 27 and to the desired angle relative to the lower surface of the footplate or a blade having an angulated cutting edge may be employed. Although not shown, the knife may have an additional locking mechanism for locking the holder 51 in the desired position relative to the handle 23. The end of the blade that extends further from the bottom of the footplate is located at the zone 113 to insure that the bottom of the incision follows the underlying corneal curve. The cutting edge of the blade then is pressed into the cornea causing a radial incision 115 to be made between zones 111 and 113. Further, inward pressing causes the footplate 27 to engage the cornea and then flatten the cornea to establish that the depth of the incision is equal to the extension of the blade below the bottom of the footplate and to obtain an incision equal to the entire length of the cutting edge of the blade.

Referring to FIGS. 8 and 9, there are illustrated flared blades as seen from the side with their cutting edges straight. FIG. 10 illustrates a blade with an angulated cutting edge relative to the straight side edges of the blade.

A rectangular blade may encounter problems in that unless it is angulated relative to the bottom of the footplate, it may produce a shortened incision of the order of 60 microns at each end due to applanation of the corneal surface as shown in FIG. 11. The flared blade of FIG. 8 avoids the problem in that it compensates for the shortening of the incision in the deepest part of the incision due to applanation. In this respect the blade of FIG. 8 provides angulation outward which when used with a jiggle will cut the initially uncut angulated deep portion of the incision. The angle theta necessary to do this preferably is about 53 degrees although it could be 85–80 degrees. The blade of FIG. 8 may have a lower cutting edge LCE no longer than about 2–3 mm. in length, two side cutting edge portions SCE 100 microns in length and two blunt non cutting edge portions BE. In one embodiment the cutting edge of the blade of FIG. 8 is 2.5 mm in length.

The length of the lower cutting edges CE of each of the blades of FIGS. 9–10 also may be no greater than 3 mm. and may be of the order of about 2.5 mm. The thickness of each of the blades of FIG. 8–10 may be of the order of 100 microns. With the angulated cutting edge CE of the blade of FIGS. 9 and 10, angular adjustment of the blade in the holding member 51 relative to the bottom of the footplate 27 to compensate for the increase in thickness of the cornea outward is not necessary.

The blades of FIGS. 8–10 may be formed of stainless steel with their cutting edges formed of gemstone such as diamond. The blades may be held in the opening by means other than the pin 85.

In a preferred embodiment, the cutting edge of the blade of FIG. 8 will have a length of about 2.5 mm. with a sharp cutting edge along its entire extent. The blade will have a flared profile with theta preferably being theoretically maximally about 53 degrees but probably may be 85–80 degrees with a cutting edge along SCE of 100–150 microns at each end. The cutting edge of the blade is to be formed of diamond with a thickness of 100 microns. The knife will have an applanation foot plate 27 having a length equal to or greater than the length of the cutting edge of the blade with a central opening 29 to allow the blade to pass through.

Figure 7:
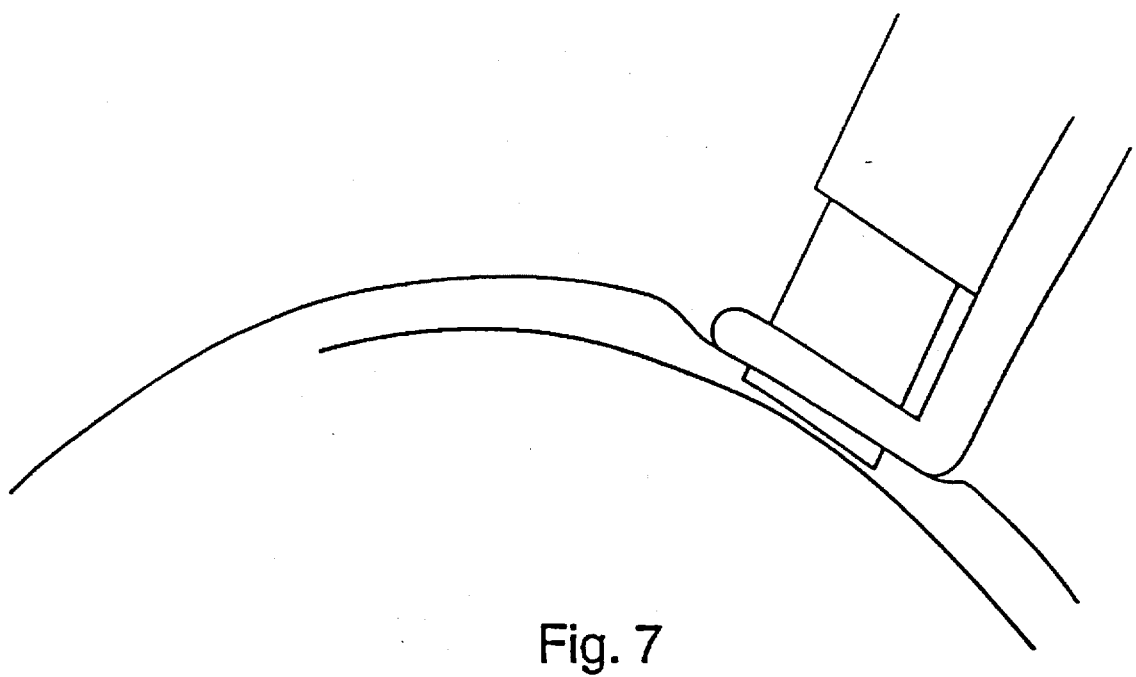
FIG. 7 illustrates use of the knife in forming radial incisions in the cornea of the eye.

If the blades of FIGS. 7 and 8 are used for making radial incisions their cutting edges will be angulated relative to the bottom of the footplate by adjustment of the knife of FIG. 1. If the blade of FIGS. 9 and 10 are used, no adjustment will be necessary, the angulation being fixed. For FIGS. 9 and 10, alpha will be about one to two degrees.

Referring now to FIGS. 19–22 the knife comprises an elongated handle 171 with a forward portion 173 having a blade supporting holding member 175 attached thereto. The member 175 has a thin extension 177 to which a footplate 179 is attached such that the footplate 179 is transverse to the extension 177. The footplate 179 has a slot 181 formed therethrough with the tip portion of the extension 177 having a slot 183 formed therethrough. The member 175 also has a slot 185 formed therein. A thin blade 187 is provided which is secured to a base 191. The blade 187 and thin base 191 are secured to the member 175 by locating the blade 187 in the slot 183 and fitting and gluing the base 191 in the slot 185. Thus the blade 187 and base 191 are securely fixed or attached to the handle or body 171, 173, 175 and cannot be moved relative to the body 171,173, 175 for adjustment purposes.

Figure 13:
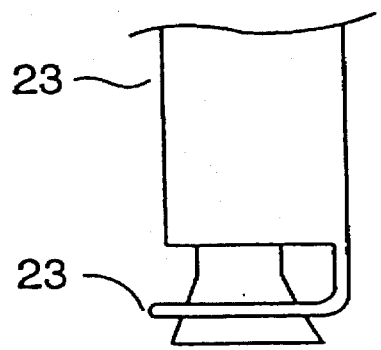
FIG. 13 illustrates a knife employing the blade of FIG. 8.
Figure 14:
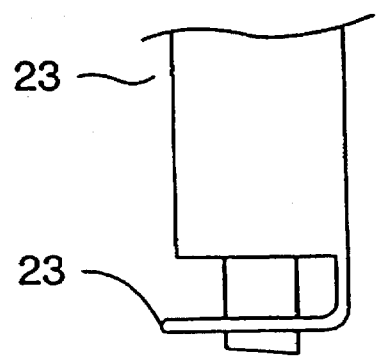
FIG. 14 illustrates a knife employing the blade of FIG. 10.
Figure 15:
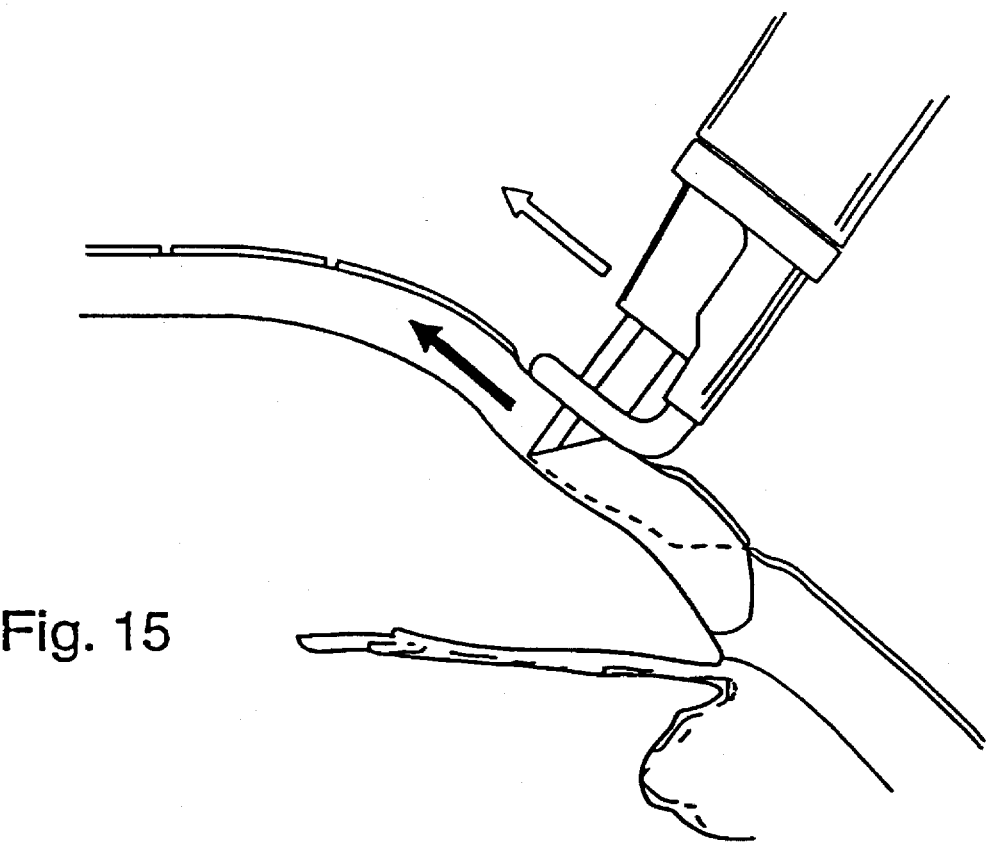
FIG. 15 is an incision profile made by the Russian cutting technique.
Figure 16:
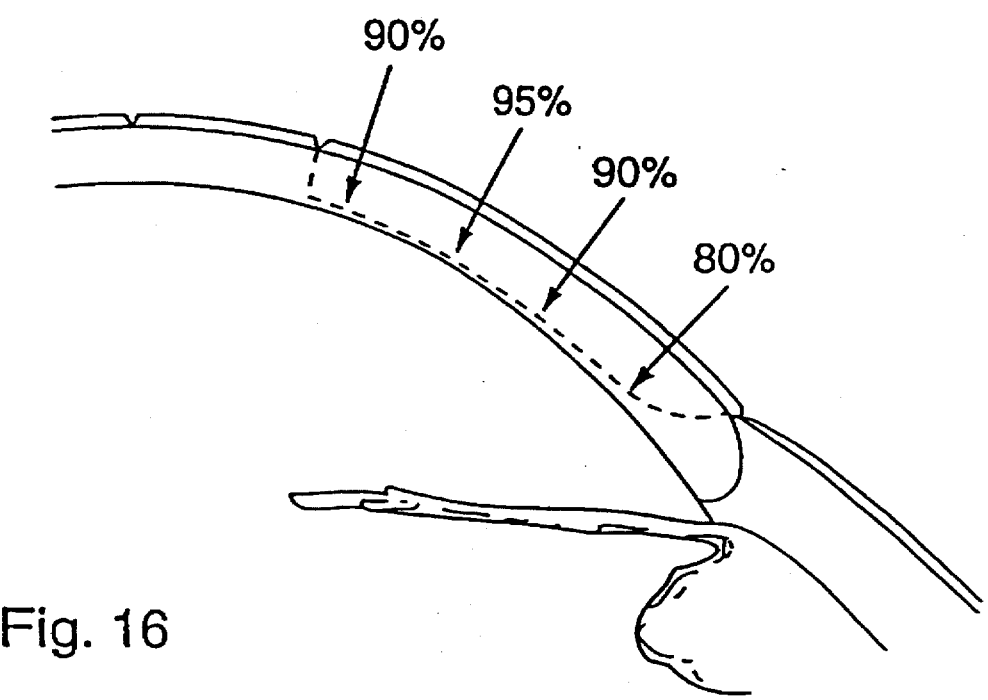
FIG. 16 is an incision profile of a completed incision made by the Russian cutting technique.
Figure 17:
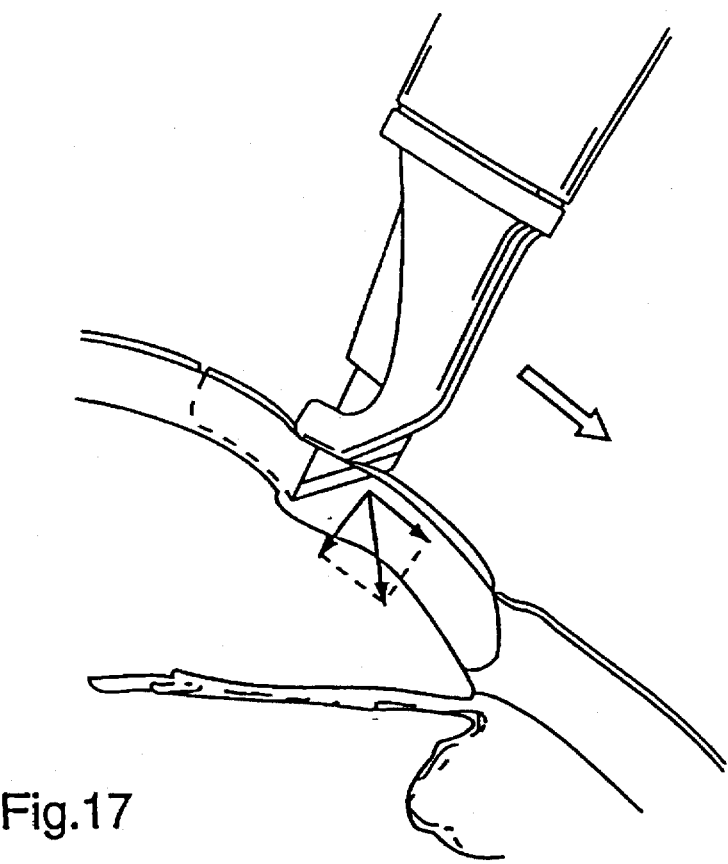
FIG. 17 is an incision profile made by the American cutting technique.
Figure 18:
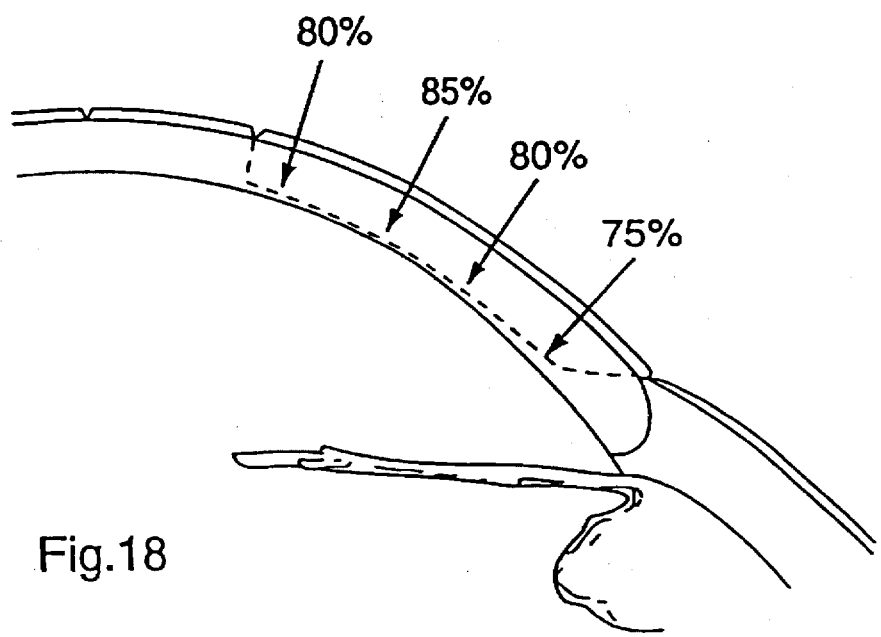
FIG. 18 is an incision profile of a completed incision made by the American cutting technique.
Figures 19, 20, 21, 22:
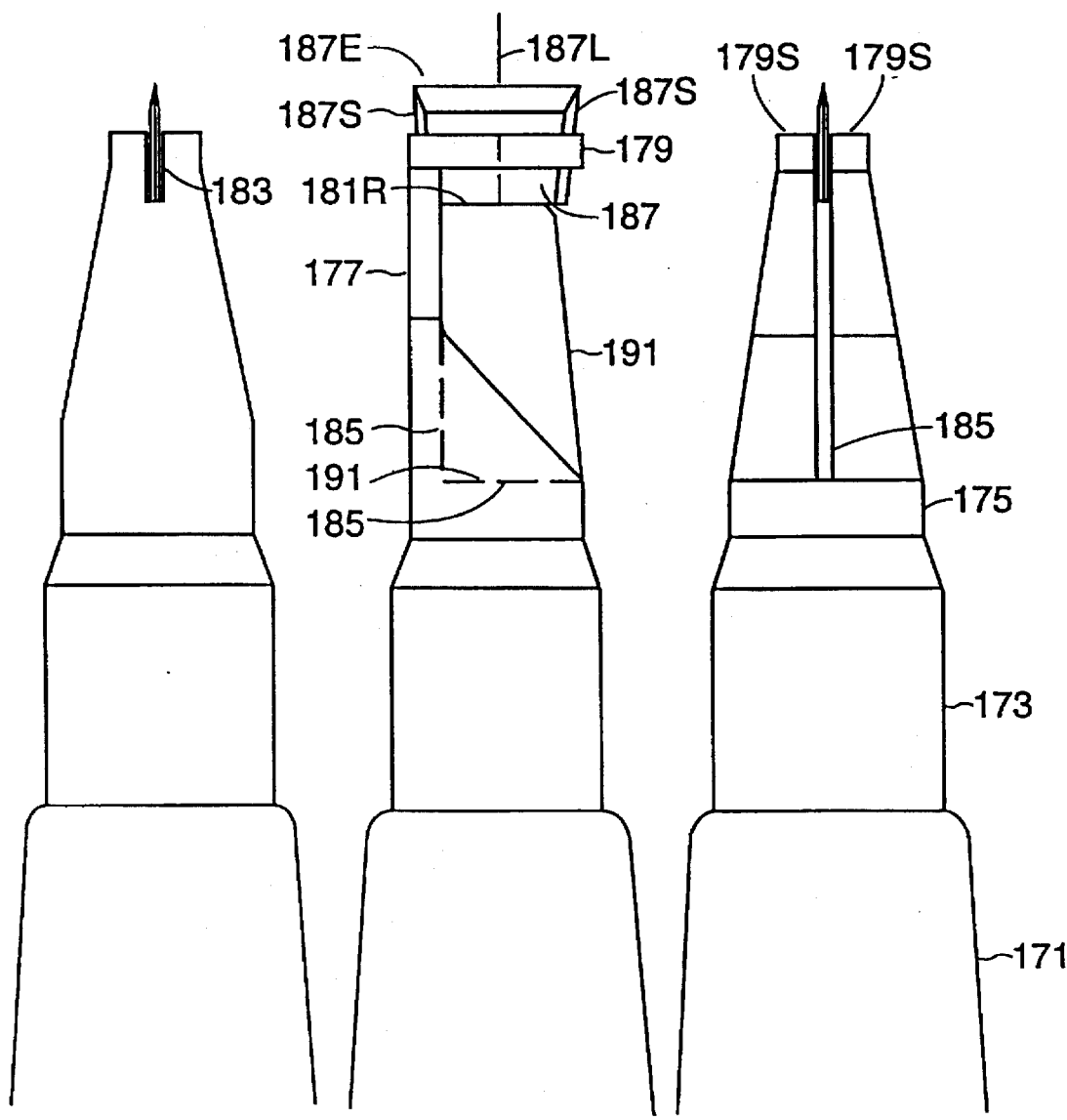
FIG. 19 is an embodiment of the invention wherein the blade is fixed to the handle of the knife.
FIG. 20 is a view of FIG. 19 as seen from the left side of FIG. 19.
FIG. 21 is a view of FIG. 19 as seen from the right side of FIG. 19.
FIG. 22 is a view of FIG. 19 as seen from the front end of FIG. 19.

The blade 187 may be formed of diamond and the base 191 may be formed of a suitable metal. The members 171, 173, 175, 177, and 179 also may be formed of a suitable metal. The foot plate 179 has a flat forward surface 179S on opposite sides of the slot 181. The blade 187 has a forward cutting edge 187E and two side cutting edges 187S. In the position shown in FIGS. 19–22, the cutting edge 187E of the blade 187 extends beyond the surface 179S of the footplate and is parallel to the surface 179S. The forward portions of the side cutting edges 187S also extends beyond the surface 179S. The side edges 187S of the blade flare outward from the rear edge 187R relative to a central line 187L in the same manner as described with respect to the blade of FIG. 8 and 13. The knife is used in the same manner as previously described with respect to embodiments of FIGS. 1–8, and 13 such that the blade edge 187E is pressed against the cornea for cutting purposes until the footplate surface 179S bears against the cornea.

Figures 23, 24, 25:
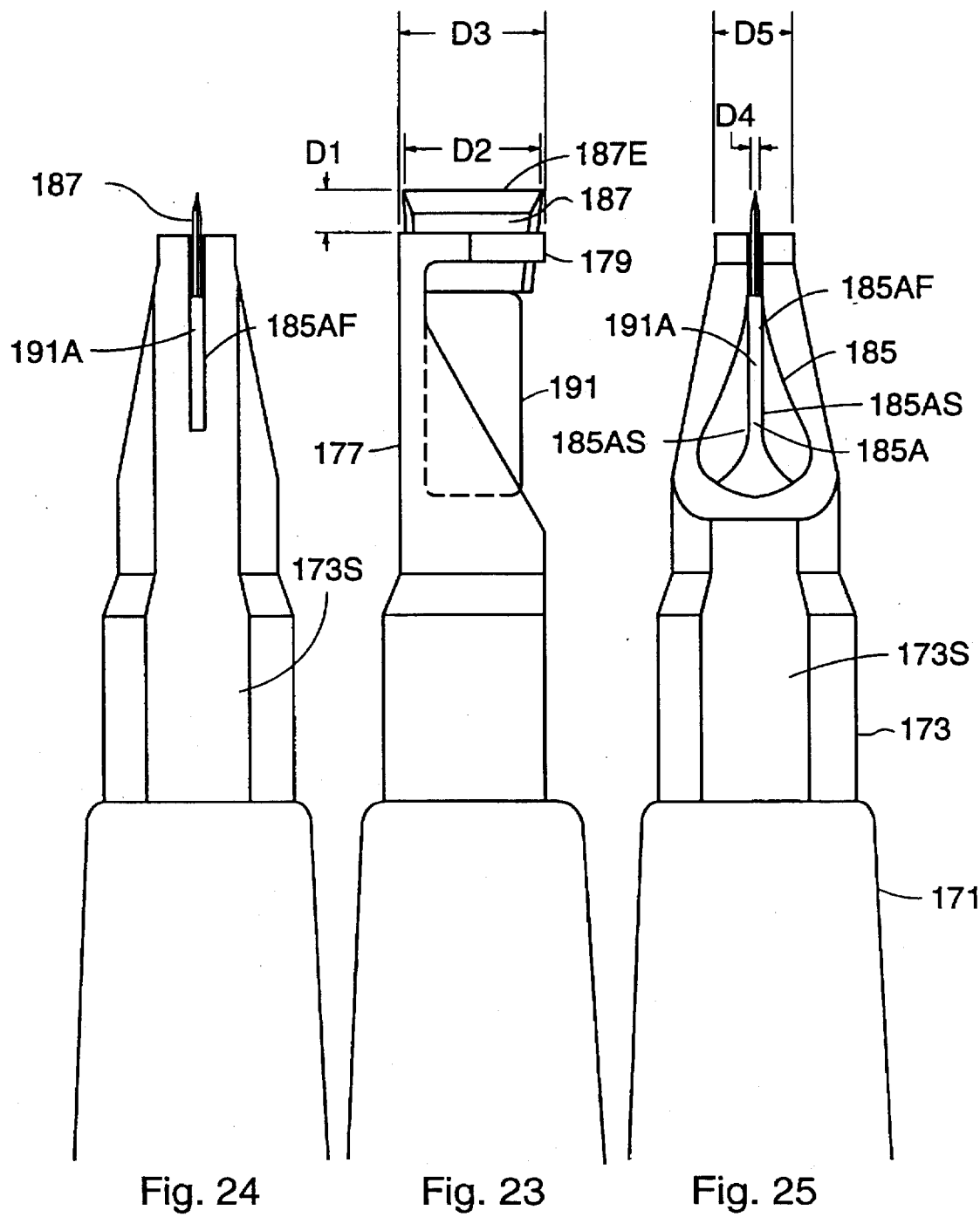
FIG. 23 is a modification of the knife of FIGS. 19–22.
FIG. 24 is a view of FIG. 23 as seen from the left side of FIG. 23.
FIG. 25 is a view of FIG. 23 as seen from the right side of FIG. 23.

The embodiment of FIGS. 23–25 is similar to that to FIGS. 19–22 except that the slot 185 is tear shaped on one side as shown in FIG. 25 and tapers inward to a horn shaped slot 185A having sides 185AS. The forward straight portion 185AF of the slot 185A extends through the member 175 on the other side as shown in FIG. 24. The base 191A also is horn shaped and is fitted and glued into the slot 185A to securely hold the base and the blade 187 in the slot 185 with its edge 187E extending beyond the surfaces 179S of the footplate 179. Thus the blade 187 and base 191A are securely fixed or attached to the handle 171,173, 175 and cannot be moved relative to the handle 171, 173, 175 for adjustment purposes. The member 175 also has two flat sides 175S. The knife is used in the same manner as previously described with respect to the embodiments of FIGS. 1–8, and 13 such that the blade cutting edge 187E is pressed against the cornea for cutting purposes until the footplate surface 179S bears against the cornea.

In the embodiment of FIGS. 26–27 the holding member 275 has a flat surface 279S with a slot 285 formed therein for receiving the blade 187. The slot 285 has a narrow portion 285N into which the end of the blade 187 is fitted and glued for securely holding the blade in place to members 275, 175, 171 with its curing edge 187E extending beyond the surface 279S which forms a footplate which will bear against the cornea during the cutting operation.

The blade 187 is the same in all three embodiments of FIGS. 19–30. In one embodiment, the dimensions D1, D2, D3, D4, and D4 are as follows:

D1=600 microns

D2=3.00 mm±0.1

D3=3.2 mm±0.1

D4=0.1 mm±0.2

D5=1.4 mm±0.2

Figures 32, 33, 34:
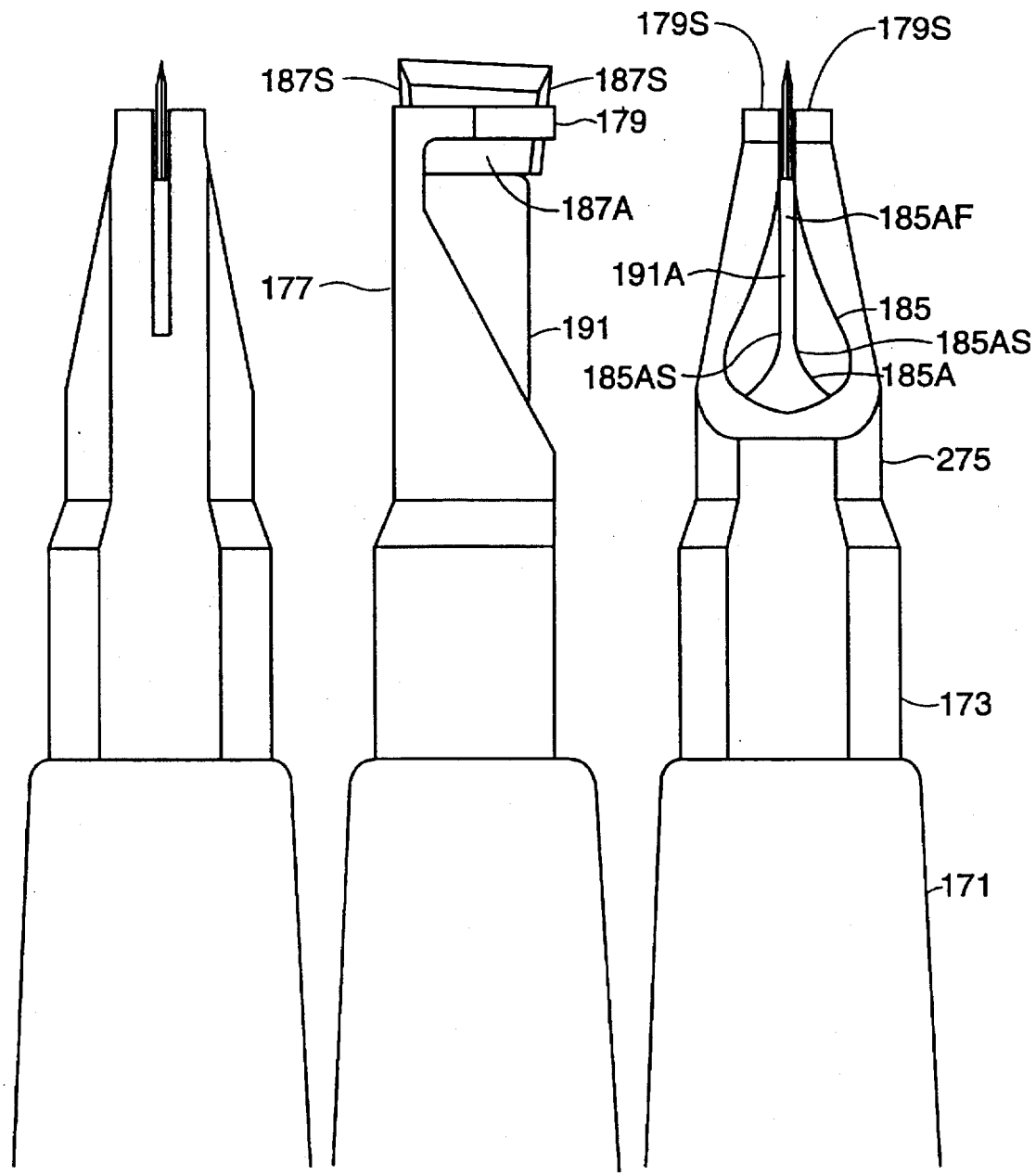
FIGS. 32–34 illustrate the knife of FIGS. 24–25 with a blade having an angulated cutting edge secured to the body of the knife.

Referring to FIGS. 32–34 the knife is the same as that of FIGS. 24–25 except that the blade 187A has an angulated cutting edge 187EA which forms a small acute angle relative to the footplate surface 179S when the base 191 and the blade are secured to the body 171,173. Except for the angulated cutting edge 187EA, the blade 187A is the same as that of FIGS. 19–27. The blade 187A also may be used in the embodiments of FIGS. 19–22 and 26–29 such that its angulated cutting edge 187EA forms a small acute angle relative to the footplate surfaces 179S and 279S respectively.

I claim:

1. A refractive surgery keratotomy knife, comprising:

a support body having a footplate with first and second opposite facing sides, said footplate having a bottom surface on said second side to be place against the cornea of the eye, a thin planar blade having a main cutting edge which is substantially straight and which has a given length, said blade has an attachment portion and two opposite side edges extending from said attachment portion, each of said side edges has a substantially straight side cutting edge which forms an acute angle relative to the length of said main cutting edge, said opposite side edges extend away from each other from said attachment portion to said main cutting edge, a blade holding member coupled to said attachment portion of said blade for supporting said blade in a position to extend from said first side beyond said second side of said footplate with said main cutting edge being located on said second side spaced from said bottom surface of said footplate for surgery incision purposes.

2. The refractive surgery keratotomy knife of claim 1, wherein:

said bottom surface of said footplate is substantially flat, said main cutting edge of said blade is substantially parallel to said bottom surface of said footplate.

3. The refractive surgery keratotomy knife of claim 1, wherein:

said bottom surface of said footplate is substantially flat, said main cutting edge of said blade forms an acute angle relative to said bottom surface of said footplate.

4. The refractive surgery keratotomy knife of claim 1, wherein:

said blade has a center line between said two opposite side edges with each of said two opposite side edges extending away from said center line at an angle less than 37°.

5. The refractive surgery keratotomy knife of claim 1, wherein:

said blade has a center line between said two opposite side edges with each of said two opposite side edges extending away from said center line at an angle of about 10°.

6. The refractive surgery keratotomy knife of claim 2, wherein:

said blade has a center line between said two opposite side edges with each of said two opposite side edges extending away from said center line at an angle less than 37°.

7. The refractive surgery keratotomy knife of claim 3, wherein:

said blade has a center line between said two opposite side edges with each of said two opposite side edges extending away from said center line at an angle less than 37°.

8. The refractive surgery keratotomy knife of claim 1, wherein:

said footplate comprises two spaced apart footplate portions coupled to two spaced apart support portions respectively with said blade holding member extending between said two spaced apart support portions and said blade supported to extend between said two spaced apart footplate portions.

9. The refractive surgery keratotomy knife of claim 4, wherein:

said footplate comprises two spaced apart footplate portions coupled to two spaced apart support portions respectively with said blade holding member extending between said two spaced apart support portions and said blade supported to extend between said two spaced apart footplate portions.

* * * * *